United States Patent [19]
Miller et al.

[11] Patent Number: 5,498,373
[45] Date of Patent: Mar. 12, 1996

[54] PROCESS FOR REDUCING THE LEVELS OF NITRITE CONTAMINANTS IN AMINE OXIDE SURFACTANTS

[75] Inventors: Larry E. Miller, Cincinnati; Gene P. Hawkins, Oregonia; Bernard G. Durham, Mason, all of Ohio

[73] Assignee: The Procter & Gamble Company, Cincinnati, Ohio

[21] Appl. No.: 472,793

[22] Filed: Jun. 7, 1995

Related U.S. Application Data

[60] Division of Ser. No. 286,844, Aug. 5, 1994, which is a continuation-in-part of Ser. No. 145,257, Oct. 29, 1993, abandoned.

[51] Int. Cl.$^6$ ............................ C07C 291/04; C11D 1/75
[52] U.S. Cl. ...................... 252/546; 252/541; 252/544; 252/545; 252/547; 564/2; 564/297; 564/298
[58] Field of Search ........................... 564/2, 297, 298; 252/541, 544, 545, 546, 547

[56] References Cited

U.S. PATENT DOCUMENTS

| | | | |
|---|---|---|---|
| 3,283,007 | 11/1966 | Chadwick | 260/583 |
| 4,247,480 | 1/1981 | Murata et al. | 564/298 |
| 5,075,501 | 12/1991 | Borland et al. | 564/297 |

FOREIGN PATENT DOCUMENTS

320694A2  6/1989  European Pat. Off. ...... C07C 135/02

*Primary Examiner*—Peter O'Sullivan
*Attorney, Agent, or Firm*—Robert B. Aylor; Jerry J. Yetter

[57] ABSTRACT

Amine oxide surfactants contaminated with nitrite are treated under acidic conditions with materials such as maleic acid and diethylenetriaminepentaacetate (DTPA) to reduce nitrite levels below 1 ppm. Thus, $C_{12-13}$ dimethyl amine is oxidized with hydrogen peroxide in the presence of maleic acid and DTPA to reduce nitrite levels. The resulting nitrite-free amine oxide is employed in various detergent compositions.

1 Claim, No Drawings

PROCESS FOR REDUCING THE LEVELS OF NITRITE CONTAMINANTS IN AMINE OXIDE SURFACTANTS

This is a division of application Ser. No. 08/286,844, filed on Aug. 5, 1994; which is a continuation-in-part of application Ser. No. 08/145,257, filed Oct. 29, 1993, now abandoned.

FIELD OF THE INVENTION

The present invention relates to an improvement in a chemical process for preparing amine oxide surfactants, whereby the content of nitrite contaminants is reduced or substantially eliminated for an extended period of time.

BACKGROUND OF THE INVENTION

The preparation of amine oxide surfactants by the oxidation of tertiary amines is of considerable commercial interest. Such surfactants are widely used in commercial cleaning compositions, especially high sudsing dishwashing detergents. However, it has now been discovered that some sources of amine oxide surfactants may be contaminated with residual amounts of nitrite materials, especially inorganic nitrites. Contamination by such nitrites may be tolerable under many circumstances. For some uses, however, the presence of nitrites may be undesirable, since they prospectively can react with other ingredients which may be present in fully formulated detergent compositions.

Detergent formulators presumably could arrange for special care to be taken during the manufacture of amine oxides in order to minimize the formation of undesirable nitrite contaminants. However, the manufacturer [formulator] of high volume, low-cost chemicals such as home-use detergents can ill-afford surfactants and other raw materials requiring special reaction techniques or special reactants, due to their expense.

The present invention solves the problem of contamination of amine oxide surfactants by nitrite materials using simple, cost-effective techniques. The invention herein thus affords access to a high quality supply of this class of surfactants.

BACKGROUND ART

The synthesis of amine oxides is described in Kirk-Othmer "Encyclopedia of Chemical Technology" 3rd Edition Vol. 2 pp. 264–266, John Wiley and Sons 1978, in "Surfactant Science Series" Vol. 1 Nonionic Surfactants, M. J. Schick, editor, Marcel Dekker, Inc. 1966 pp. 403–407, and in U.S. Pat. No. 3,283,007, issued Nov. 1, 1966 to A. F. Chadwick.

SUMMARY OF THE INVENTION

The present invention encompasses, in a process for preparing amine oxide surfactants of the formula R R$^1$ R$^2$ N→O wherein R is a C$_8$ to C$_{18}$ alkyl or alkenyl substituent and R$^1$ and R$^2$ are each C$_1$–C$_4$ alkyl or hydroxyalkyl substituents by the oxidation of the corresponding amine of the formula R R$^1$ R$^2$ N, the improvement which comprises conducting the oxidation in the presence of polycarboxylate material, whereby contamination of the amine oxide surfactant by nitrites is substantially decreased for an extended period of time. The polycarboxylate material is preferably citrate or a chelating compound comprising a chelating active selected from the group consisting of water-soluble ethylenediamine tetraacetates (EDTA), diethylenetriaminepentaacetates (DTPA), nitrilotriacetates and mixtures thereof and a chelating co-active selected from the group consisting of malates, maleates, succinates, and mixtures thereof. In a preferred mode, the amine reactant is a C$_{10}$–C$_{18}$ alkyl dimethylamine.

The oxidation step herein is preferably conducted using hydrogen peroxide or source of hydrogen peroxide, or by hydrogen peroxide generated in situ.

When conducted in the presence of carboxylate chelants, the process is preferably carried out at a pH in the range of from about 6 to about 8. The process can also advantageously be carried out in the presence of sulfamic acid, which typically can comprise 0.2%–5% of the amine being oxidized.

The use of a single polycarboxylate material, such as DTPA, decreases the nitrite level in amine oxide to acceptable levels, under 3. ppm. However, it has now been discovered that, with the exception of citrate, when only a single polycarboxylate material is used to decrease nitrite levels, the nitrite level rebounds within a few days at ambient temperature. It is therefore preferable to use either citrate or polycarboxylate material that is a chelating compound comprising specific chelating active and specific chelating co-active or mixtures thereof, as set forth above.

An overall process according to this invention is wherein:

a. the amine is a C$_{12}$–C$_{16}$ alkyl dimethylamine;

b. the oxidation is conducted using hydrogen peroxide;

c. the oxidation is conducted in the presence of citrate or water-soluble DTPA, EDTA, nitriloacetate, or mixture thereof in combination with water-soluble maleate, malate, succinate, citrate, or mixtures thereof;

d. the oxidation is conducted at a pH in the range of from about 6 to about 8; and e. the oxidation is conducted over a temperature range of from about 50° C. to about 75° C.; whereby the resulting amine oxide has a nitrite content below about 3 ppm for at least about 4 weeks.

It is to be understood that citric acid alone (without an additional chelating co-active) gives the desired result. With maleate alone, optimal, low nitrite levels are approached, but not consistently achieved without DTPA. Excluding citrates, it is necessary to combine specific chelating active and specific chelating co-active in order to obtain long-term nitrite level below about 3 ppm.

The invention thus provides stable detergent compositions (especially liquid compositions) comprising amine oxide detergent surfactant prepared in the foregoing manner.

All percentages, ratios and proportions herein are by weight, unless otherwise specified. All documents cited are incorporated here by reference.

DETAILED DESCRIPTION OF THE INVENTION

For purposes of clarity, the following defines the terms used herein.

By "nitrite" herein is meant the NO$_2$- species, including all forms of nitrous acid or its salts or reactive derivatives such as HNO$_2$, NaNO$_2$, N$_2$O$_3$, H$_2$NO$_2^+$, N$_2$O$_4$, NO$^+$, or related species.

By "diminished in", "substantially diminished in", or "substantially free of" nitrite, or like terms used herein is meant that the nitrite-contaminated amine oxide surfactant which has been treated according to the present invention thereafter contains, "as made", no more than about 3 ppm, preferably no more than about 1 ppm, most preferably zero ppm nitrite, as measured by standard nitrite analyses. By "polycarboxylates" such as "citrate", "malate", "maleate" or the like herein is meant the free acid, the soluble salt, the anhydride, or any other suitable source of the polycarboxylate material. For example, maleic anhydride is more economically available on a commercial scale than the free acid and is preferred herein.

Amine Oxide Synthesis

As described in the references cited above, alkyldimethylamine oxide surfactants are produced by oxidizing the desired alkyldimethylamine with hydrogen peroxide, which is generally in the form of a 5% to 70% aqueous solution. Although less can be used, typically the hydrogen peroxide is used at about a 5% to 10% excess of the stoichoimetric amount when conversion of more than 99% of the tertiary amine is required. It is preferable in the present invention to use peroxide levels of from about 95% to about 125% of the stoichiometric amount, more preferably from about 100% to about 115%, of the stoichiometric amount, and to conduct the process at a temperature of from about 40° C. to about 100° C., preferably from about 50° C. to about 85° C., and more preferably from about 50° C. to about 75° C.

The reaction can be carried out in the presence of an organic solvent such as ethyl or isopropyl alcohol. Use of an organic solvent enables production of higher concentrations of amine oxide while avoiding gel formation. A catalyst can be used in the reaction of the present invention to accelerate the reaction rate. Total reaction time is typically 2 to 20 hours depending on reaction stoichiometry, catalyst, solvent system and degree of tertiary amine conversion required. Commercially, either batch or continuous reaction processes are used. If desired, peroxide reaction residues can be reduced or eliminated by adding a reducing agent, such as sodium sulfite, or other agent to promote peroxide decomposition. However, such peroxide residues can be beneficial for the reduction of nitrite levels under acidic conditions. In fact, it has now been discovered that color stability can be affected by residual peroxide levels. In order to obtain a color stability benefit, residual peroxide levels should be from about 0.02% to about 0.09%, preferably from about 0.03% to about 0.08%, more preferably from about 0.04% to about 0.07%, by weight of the total $H_2O_2$.

Some amine oxide surfactants prepared in the foregoing, standard manner have now been found to be contaminated with as much as 60 ppm of nitrite. By the present procedures, these nitrite levels can be lowered to 1–3 ppm, or less.

Present Process

In the process of this invention the oxidation of the amine is carried out using otherwise conventional procedures, as noted above, but with the addition of the polycarboxylate material.

Polycarboxylate Material

The use of a single polycarboxylant material, with the exception of citrate, such as DTPA, decreases the nitrite level in amine oxide to acceptable levels, under 3. ppm. However, it has now been discovered that when only a single polycarboxylate material is used to decrease nitrite levels, the nitrite level rebounds within a few days at ambient temperature. It is therefore preferable to use citrate or polycarboxylate material that is a chelating compound comprising specific cheating active and specific chelating co-active.

Said chelating active is selected from the group consisting of water-soluble (EDTA), (DTPA), nitrilotriacetates and mixtures thereof and said chelating co-active selected from the group consisting of malates, maleates, succinates, and mixtures thereof. Preferably said chelating active is selected from the group consisting of EDTA and DTPA and said chelating co-active is selected from the group consisting of malates and maleates, more preferably said chelating active is DTPA and said chelating co-active is maleic acid.

Typically, the amount of citrate or chelating compound, (chelating active+ chelating co-active) is from about 0.1% to about 6%, preferably from about 0.25% to about 5%, more preferably from about 0.5% to about 4%, by weight of the amine. The ratio of chelating active to chelating co-active typically is from about 1:20 to about 2:1, preferably from about 1:15 to about 1:5, more preferably from about 1:10 to about 1:1.

Thus, in a preferred process DTPA and maleic acid (typically 1:5 to 5:1 by weight) are dissolved in the reaction mixture. The pentasodium form of DTPA, available as DOW VERSENEX 80, is especially useful herein, but either acid or salt forms work.

Storage

It has been discovered that storage temperature is also responsible for the rebounding of nitrite levels as well. Elevated temperatures, i.e., above about 50° C., cause increased nitrite levels in the production materials of the present invention. Therefore, it is preferably to keep the resulting product of the present invention at typical ambient temperature levels, i.e., from about 25° C. to about 49° C.

Nitrite Analyses

The presence of nitrites in the amine oxide surfactants, both before and after use of the procedures of this inventions, can be measured in several ways. The following are illustrative.

a) Nitrite test strips, sold under the trademark E. M. Quant, Catalog number 10007-1 (Division of EM Industries, Inc., Gibbstown, N.J.) are used in standard fashion as directed by the manufacturer. These test strips are convenient and quite suitable under most conditions.

b) If more precise measurement is needed, nitrite can be assayed spectrophotometrically (Varian Spectrophotometer Model 219) using a colorimetric assay with sulfanilamide reagent (5 g. sulfanilamide, 60 ml conc. HCl diluted to 500 ml in $H_2O$) and N-(1-naphthyl)-ethylene-diamine dihydrochloride "NED" (500 mg diluted to 500 ml in $H_2O$; stored in a dark bottle and replaced if the solution develops a strong brown color). The test employs a 5 ml test solution of the amine oxide surfactant at 3–30% concentrations, depending on nitrite concentration. In the test, 0.1 ml of the sulfanilamide reagent is added to the amine oxide solution. After 5 minutes, the pH is adjusted to 1.0–1.5 using HCl. Then, 0.1 ml of the NED solution is added. Color develops fully within a few hours. The absorbance is measured at 543 nanometer (nm) wavelength. The results are compared with samples to which known amounts of nitrite have been intentionally added.

(c) In cases where a large excess of nitrite scavenger is present, nitrite concentration can be determined by chromatographic separation methods, either by ion exchange chromatography or capillary zone electrophoresis.

The following illustrates the nitrite reduction procedure of the present invention.

EXAMPLE I 10 grams of maleic acid and 3.75 grams of VERSENEX 80, a 40% by weight aqueous solution of the sodium form of DTPA, are added to 523 grams of distilled water. 157 grams of 30% aqueous hydrogen peroxide are added and stirred. The mixture is heated to 50° C., 219 grams of $C_{12}$–$C_{16}$ alkyldimethylamine are added. The pH of the mixture at this point is 8.0. Stirring is continued at 50° C. for two hours followed by an additional five hours at 70° C. The 963 grams of reaction product contain 28% amine oxide. The pH of the reaction product is 6.9. No nitrite is detected with E. M. Quant test strips. After a week's storage at ambient conditions, the reaction product has no detectable nitrite using the test strip method and 0.6 ppm measured using ion chromatography.

EXAMPLE II 7.4 grams of sulfamic acid and 4.4 grams of the acid form of DTPA are added to 1659 grams of water. 471 grams of 30% hydrogen peroxide are then added and stirred. The mixture is heated to 50° C. while stirring. Upon reaching 50° C., 867 grams of $C_{12}$–$C_{16}$ alkyldimethylamine are added. Stirring is continued for two hours at 50° C. followed by 5 hours at 70° C. The reaction product contains 31% amine oxide and no nitrite is detected with test strips. The pH of the reaction product is 7.6. After a week's storage at ambient conditions, the reaction product contains 5 ppm nitrite measured using the test strip method and 6.5 ppm measured by ion chromatography.

EXAMPLE III 10 grams of maleic acid are added to 527 grams of distilled water. 157 grams of 30% aqueous hydrogen peroxide are added and stirred. The mixture is heated to 50° C. while stirring. Upon reaching 50° C., 219 grams of $C_{12}$–$C_{16}$ alkyldimethylamine are added. Stirring is continued at 50° C. for two hours followed by an additional five hours at 70° C. The reaction product contains 28% amine oxide. The pH of the reaction product is 6.8. After completion of the reaction no nitrite is detected with the test strips. After a week storage at ambient conditions, the reaction product contains 5 ppm nitrite measured using the test strip method and 3.2 ppm measured by ion chromatography.

EXAMPLE IV 157 grams of 30% aqueous hydrogen peroxide are added to 537 grams of distilled water and stirred. The mixture is heated to 50° C. while stirring. Upon reaching 50° C., 219 grams of $C_{12}$–$C_{16}$ alkyldimethylamine are added. Stirring is continued at 50° C. for two hours followed by an additional five hours at 70° C. The pH of the reaction product is 7.6. After completion of the reaction, 20 ppm nitrite is measured using the test strip method.

The following data illustrate the results secured in the manner disclosed above.

| Description | "As Made" Test Strip | Nitrite (ppm) Test Strip Days Later | Ion Chromatography |
|---|---|---|---|
| Laboratory Control #1 (0.25% sulfamic acid) | 20 | | |
| Laboratory Control #2 (0.25% sulfamic acid) | 30 | | |
| Laboratory Control #3 (0.25% sulfamic acid) | 20 | | |
| Anion exchange treated control #2 | ND | | |
| 3% sulfamic acid | 10 | | |
| 5% ethanol (35% AO active) | 5 | | |
| 1% maleic acid, no sulfamic acid | <2 | 5 | 3.2 |
| 0.5% maleic acid, no sulfamic acid | 2 | | |
| 0.375% maleic acid, no sulfamic acid | 5 | | |
| 0.25% maleic acid, no sulfamic acid | 10 | | |
| 1% maleic acid, 0.25% sulfamic acid | <2 | | |
| 0.06% DTPA, 0.25% sulfamic acid | ND | 3 | |
| 0.06% DTPA, 0.25% sulfamic acid, city water | ND | <2 | 3.3 |
| 0.6% DTPA, no sulfamic acid, city water | 2 | 7–8 | |
| 0.15% DTPA, no sulfamic acid, city water | ND | 2 | 5.7 |
| 0.15% DTPA, 0.25% sulfamic acid, city water | <2 | 2–5 | 6.5 |
| 0.25% citric acid, no sulfamic acid | 2 | | |
| 1% citric acid, no sulfamic acid | ND | ND | |
| 2% citric acid, no sulfamic acid | ND | ND | ND |
| 0.15% DTPA, 1% maleic acid, no sulfamic acid | ND | ND | 0.6 |

ND = none detected
For nitrites: <~2 ppm by test strips; <0.5 ppm by ion chromatography)

DETERGENT FORMULATIONS

Surfactants and Suds Enhancers - The substantially nitrite-free amine oxide surfactants afforded by the present invention are useful in any circumstance where the prospective reaction of nitrite with the detersive ingredients is desirably avoided. The amine oxides herein are especially preferred for use in liquid detergents, especially those containing nitrogen compounds like amines and/or amides.

The following is intended to illustrate the use of the amine oxide surfactants made in accordance with this invention in liquid detergent compositions, but is not intended to be limiting thereof. Water-soluble $Ca^{++}$ or $Mg^{++}$ salts, e.g., $MgSO_4$, $MgCl_2$ or the like can be used to introduce such cations into the compositions, typically at levels of 0.01%–2%, to enhance sudsing and grease removal performance.

EXAMPLE V

Homogeneous light duty liquid detergent compositions which are especially adapted for dishwashing and other hard surface cleaning operations are as follows. In the Examples A–D, the surfactants comprise various alkyl ethoxy sulfate surfactants which, using standard terminology, are abbreviated to indicate their average degree of ethoxylation; thus $C_{12-13}$ EO(0.8) sulfate indicates a sulfated mixed $C_{12}$–$C_{13}$ alcohol fraction having an average degree of ethoxylation of 0.8. These anionic ethoxy sulfates are preferably used in their $Na^+$ or $NH_4^+$ salt form. The $C_{12}$–$C_{13}$ amine oxide is a mixed $C_{12-14}$ (average) dimethyl amine oxide. The amine oxide is treated in the manner of Examples I, II III and IV, herein, $_{14}$AP betaine is $C_{12/14}H_{25/29}CONH(CH_2)_3N+(CH_3)_2\text{-}CH_2CO_2H$. The $C_{12-14}$ AP sultaine is $C_{12}/C_{14}H_{25}/_{29}CONH(CH_2)_3N+(CH_3)_2\ CH_2CH(OH)CH_2\text{-}SO_3H$. The $C_{12-14}$ DM betaine is $C_{12/14}H_{25/29}N+ (CH_3)_2CH_2CO_2H$. The ethoxylated nonionic surfactant designated $C_{9\text{-}1}EO(8)$ refers to $C_9$–$C_{11}$ alcohols ethoxylated with an average of 8 moles of ethylene oxide. The $Ca^{++}$ and $Mg^{++}$ cations are conveniently introduced into the compositions as $CaCl_2$ and $MgCl_2$. The Balance of the compositions comprises water and citrate/propylene glycol present in the glucamide surfactant (1–5%) and 1–3% cumene sulfonate or xylene sulfonate hydrotope. The pH is typically 6.8–7.4 ($NH_4^+$ salts) or 7–8.2 ($Na^+$ salts).

| Ingredient* | Percent (wt.) | | | |
|---|---|---|---|---|
| | A | B | C | D |
| $C_{12-14}$ N-methyl glucamide** | 11 | 8 | 12.7 | 9 |
| $C_{12-13}$ EO(0.8) sulfate | — | 13 | 10.0 | 9 |
| $C_{12-14}$ EO(3) sulfate | 11 | — | 2.7 | 14 |
| $C_{12-13}$ EO(6.5) sulfate | — | — | — | 3 |
| $C_{12-14}$ AP betaine | — | — | 2 | — |
| $C_{12-14}$ AP sultaine | — | — | — | 1.0 |
| $C_{12-13}$ dimethyl amine oxide | 2.5 | 3.0 | 2.5 | 1.0 |
| $C_{12-14}$ DM betaine | — | 2.0 | — | — |
| $C_{9-1}$ EO(8) | 0.5 | 8 | 7 | — |
| Ca++ | — | — | 0.5 | 1.0 |
| Mg++ | 0.9 | 0.25 | — | — |
| Balance | bal | bal | bal | bal |

*Commercial grade surfactants may be bleached to colorless (i.e., to provide water-clear liquids). The $C_{12-14}$ N-methylglucamide herein preferably has been treated with acetic anhydride in water at 60° C.–80° C. so that it contains 0.1% or less of N-methylglucamine. Optionally, for highest sudsing the glucamide surfactant can also be treated with ethanolamine at 50° C.–80° C. to reduce levels of free fatty acids to 1% or below. The amine oxide contains less than 1.0 ppm nitrite.
**Pretreated with acetic anhydride to decrease amine content.

EXAMPLE VI

A liquid detergent composition with a suds boosting fatty amide is as follows. Product pH is adjusted to 7.8 with NaOH.

| Ingredient | % (wt.) |
|---|---|
| Dimethyldodecyl amine oxide[1] | 5.0 |
| $C_{12-14}$ EO(3) sulfate | 14.0 |
| Sodium cumene sulfonate[2] | 2.0 |
| $C_{12}$ Monoethanolamide | 1.5 |
| Coconut N-methylglucamide | 7.0 |
| Water, dye, minors | Balance |

[1]Substantially nitrite free, prepared according to this invention.
[2]Introduced in acid treatment of amine oxide as sulfonic acid form and subsequently neutralized with NaOH.

In addition to the foregoing, it has now further been discovered that concentrated solutions (i.e., 31% amine oxide, and higher, typically 50–55% amine oxide) of amine oxides which are substantially free of nitrite can be prepared using the technology herein. Such concentrated solutions are especially useful in formulating the so-called concentrated or "compact" liquid detergent compositions which are now favored by many consumers and which, in general, contain lower amounts of water than conventional detergents. In the present process, the tertiary amine is oxidized in the presence of, for example, DTPA and maleic anhydride, preferably in the presence of alcohol (ethanol is preferred) or other suitable material to avoid amine oxide gelling at the higher concentrations.

The following illustrates this concentrated process in more detail.

EXAMPLE VII

A 50–55% (wt.) "high active" solution of $C_{12-14}$ dimethyl amine oxide is prepared in water/ethanol (70:30) by oxidizing the corresponding amine with peroxide, with the following results.

| Run | Nitrite (ppm) |
|---|---|
| A. High active, no additives | 7.0 |
| B. High active, 1% maleic acid, 0.15% DTPA | 0.5 |
| C. High active, 1% maleic anhydride, 0.15% DTPA | 0.2 |

While the foregoing illustrates the present invention and its use in liquid detergents, especially dishwashing compositions, it is not intended to limit the scope of the invention. The amine oxide surfactants provided by this invention can be used in any detergent composition where high sudsing, good grease/oil removal and overall product stability are desired. The invention herein can be used with various conventional ingredients to provide fully-formulated fabric laundering compositions, hard-surface cleansers, personal cleaning products and the like. Such compositions can be in the form of liquids, granules, bars and the like.

What is claimed is:

1. A stable detergent composition comprising an amine oxide surfactant of the formula R $R^1R^2N\rightarrow O$ wherein R is a $C_8$ to $C_{18}$ alkyl or alkenyl substituent and $R^1$ and $R^2$ are each $C_1$–$C_4$ alkyl or hydroxyalkyl substituents, prepared by; the oxidation, using hydrogen peroxide or a source of hydrogen peroxide, of the corresponding amine of the formula R $R^1R^2N$, which comprises conducting said oxidation in the presence of a chelating compound comprising a chelating active selected from the group consisting of water-soluble ethylenediaminetetraacetates, diethylenetriaminepentaacetates, nitriloacetates, and mixtures thereof, and a chelating co-active selected from the group consisting of malates, maleates, succinates, and mixtures thereof, wherein said process is carried out at a pH of from 6 to 8, whereby contamination of said amine oxide surfactant by nitrites is substantially decreased for at least about 4 weeks.

\* \* \* \* \*